(12) United States Patent
Justin et al.

(10) Patent No.: US 7,766,969 B2
(45) Date of Patent: Aug. 3, 2010

(54) MODULAR PROGRESSIVE IMPLANT FOR A JOINT ARTICULATION SURFACE

(75) Inventors: Daniel F. Justin, Logan, UT (US); E. Marlowe Goble, Logan, UT (US); Robert A. Hodorek, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 11/557,399

(22) Filed: Nov. 7, 2006

(65) Prior Publication Data
US 2007/0129808 A1 Jun. 7, 2007

Related U.S. Application Data

(60) Provisional application No. 60/742,539, filed on Dec. 5, 2005.

(51) Int. Cl.
*A61F 2/38* (2006.01)
(52) U.S. Cl. .................. 623/20.15; 623/20.34
(58) Field of Classification Search ............. 623/20.14, 623/20.15, 20.28–20.36, 23.44
See application file for complete search history.

(56) References Cited

U.S. PATENT DOCUMENTS

| | | | |
|---|---|---|---|
| 4,257,129 A | 3/1981 | Volz | |
| 4,479,271 A | 10/1984 | Bolesky et al. | |
| 4,822,366 A | 4/1989 | Bolesky | |
| 4,936,853 A | 6/1990 | Fabian et al. | |
| 4,944,757 A * | 7/1990 | Martinez et al. | 623/20.15 |
| 5,019,103 A | 5/1991 | Van Zile et al. | |
| 5,061,271 A | 10/1991 | Van Zile | |
| 5,092,895 A | 3/1992 | Albrektsson et al. | |
| 5,133,760 A | 7/1992 | Petersen et al. | |
| 5,194,066 A | 3/1993 | Van Zile | |
| 5,290,313 A | 3/1994 | Heldreth | |
| 5,395,401 A | 3/1995 | Bahler | |
| 5,609,641 A | 3/1997 | Johnson et al. | |
| 5,658,341 A * | 8/1997 | Delfosse | 623/20.32 |
| 5,782,920 A | 7/1998 | Colleran | |
| 5,876,459 A | 3/1999 | Powell | |

(Continued)

FOREIGN PATENT DOCUMENTS

EP    0 619 990 A1    10/1994

(Continued)

OTHER PUBLICATIONS

Search report mailed Dec. 8, 2008 in related European application No. EP08158208.2.

(Continued)

*Primary Examiner*—Corrine M McDermott
*Assistant Examiner*—Christopher D Prone
(74) *Attorney, Agent, or Firm*—Baker & Daniels LLP

(57) ABSTRACT

An implant for on a resected articulation surface of a bone includes a tray having a top surface and opposition surface. An opening extends completely through the tray between the top surface and the bone apposition surface. A bearing member is mounted on the top surface of the tray, the bearing member having a top articular surface. Anchor downwardly projects away from the bone apposition surface of the tray, the anchor being adapted to engage the bone and being configured so that the anchor can selective pass completely through the opening of the tray. A fastener connects the anchor to the tray.

18 Claims, 12 Drawing Sheets

U.S. PATENT DOCUMENTS

| | | | |
|---|---|---|---|
| 5,879,389 A * | 3/1999 | Koshino | 623/20.11 |
| 6,102,951 A * | 8/2000 | Sutter et al. | 623/18.11 |
| 6,126,692 A * | 10/2000 | Robie et al. | 623/20.32 |
| 6,139,581 A | 10/2000 | Engh et al. | |
| 6,159,216 A | 12/2000 | Burkinshaw et al. | |
| 6,162,255 A | 12/2000 | Oyola | |
| 6,168,629 B1 | 1/2001 | Timoteo | |
| 6,210,445 B1 | 4/2001 | Zawadzki | |
| 6,217,618 B1 | 4/2001 | Hileman | |
| 6,245,110 B1 | 6/2001 | Grundei et al. | |
| 6,264,699 B1 | 7/2001 | Noiles et al. | |
| 6,299,645 B1 | 10/2001 | Ogden | |
| 6,500,208 B1 | 12/2002 | Metzger et al. | |
| 6,506,216 B1 | 1/2003 | McCue et al. | |
| 6,652,587 B2 | 11/2003 | Felt et al. | |
| 6,712,855 B2 | 3/2004 | Martin et al. | |
| 6,755,864 B1 | 6/2004 | Brack et al. | |
| 6,866,683 B2 | 3/2005 | Gerbec et al. | |
| 6,869,448 B2 | 3/2005 | Tuke et al. | |
| 6,887,276 B2 | 5/2005 | Gerbec et al. | |
| 6,916,340 B2 | 7/2005 | Metzger et al. | |
| 6,923,832 B1 | 8/2005 | Sharkey et al. | |
| 6,926,738 B2 | 8/2005 | Wyss | |
| 2002/0059000 A1 | 5/2002 | Dwyer et al. | |
| 2002/0120340 A1 * | 8/2002 | Metzger et al. | 623/20.15 |
| 2003/0009232 A1 * | 1/2003 | Metzger et al. | 623/20.29 |
| 2003/0055508 A1 | 3/2003 | Metzger et al. | |
| 2003/0139817 A1 | 7/2003 | Tuke et al. | |
| 2003/0158606 A1 | 8/2003 | Coon et al. | |
| 2003/0204263 A1 | 10/2003 | Justin et al. | |
| 2003/0204268 A1 | 10/2003 | Gerbec et al. | |
| 2003/0204269 A1 | 10/2003 | Gerbec et al. | |
| 2004/0024469 A1 | 2/2004 | Ferree | |
| 2004/0073315 A1 | 4/2004 | Justin et al. | |
| 2004/0117024 A1 * | 6/2004 | Gerbec et al. | 623/18.11 |
| 2004/0122521 A1 | 6/2004 | Lee et al. | |
| 2004/0143336 A1 | 7/2004 | Burkinshaw | |
| 2004/0143337 A1 | 7/2004 | Burkinshaw | |
| 2004/0236428 A1 | 11/2004 | Burkinshaw et al. | |
| 2005/0154470 A1 | 7/2005 | Sekel | |
| 2006/0173547 A1 * | 8/2006 | Ensign | 623/20.15 |

FOREIGN PATENT DOCUMENTS

| | | |
|---|---|---|
| EP | 0 850 606 A2 | 7/1998 |
| EP | 0 884 032 A1 | 12/1998 |
| EP | 0 956 836 A1 | 11/1999 |
| EP | 0 980 679 A2 | 2/2000 |
| EP | 0 993 813 A2 | 4/2000 |
| EP | 1 234 557 A2 | 8/2002 |
| EP | 1 378 216 A2 | 1/2004 |
| EP | 1 402 857 A2 | 3/2004 |
| EP | 1 522 284 A2 | 4/2005 |
| EP | 1 550 416 A1 | 7/2005 |
| FR | 2 615 726 | 12/1988 |
| FR | 2 718 953 A1 | 10/1995 |
| WO | WO 96/23459 | 8/1996 |
| WO | WO 00/13616 | 3/2000 |
| WO | WO 00/23012 | 4/2000 |
| WO | WO 00/51528 | 9/2000 |
| WO | WO 03/061522 A2 | 7/2003 |
| WO | WO 2004/064675 A2 | 8/2004 |
| WO | WO 2004/064690 A1 | 8/2004 |
| WO | WO 2004/112650 A2 | 12/2004 |
| WO | WO 2005/025451 A2 | 3/2005 |

OTHER PUBLICATIONS

Response to the search report filed May 28, 2009 in related European application No. EP08158208.2.

* cited by examiner

MODULAR PROGRESSIVE IMPLANT FOR A JOINT ARTICULATION SURFACE

CROSS-REFERENCE TO RELATED APPLICATIONS

This application claims the benefit of U.S. Provisional Application Ser. No. 60/742,539, filed Dec. 5, 2005, which application is incorporated herein by specific reference.

BACKGROUND OF THE INVENTION

1. The Field of the Invention

The present invention relates to prosthetic joints and, more particularly, to modular interchangeable bone implants to replace articular bone surfaces and methods for installing and replacing the implants.

2. The Relevant Technology

The human body has a variety of movable orthopedic joints such as the knee joint, hip joint, shoulder joint, and the like. These joints are formed by the intersection of two bones. The intersecting end of each bone has one or more condyles consisting of a smooth articular surface that is comprised of cartilage. For example, the knee joint comprises two generally rounded condyles, i.e., lateral and medial condyles that are located at the lower or distal end of the femur. These femoral condyles are disposed above corresponding lateral and medial condyles located at the upper or proximal end of the tibia.

As a result of injury, wear, arthritis, disease or other causes, it is occasionally necessary to replace all or part of an orthopedic joint with an artificial implant. This procedure is referred to as a joint replacement or arthroplasty. For example, a total knee arthroplasty comprises cutting off or resecting the femoral condyles at the distal end of the femur and the tibial condyles at the proximal end of the tibia. Complementary artificial implants, referred to as total condylar implants, are then mounted on the distal end of the femur and the proximal end of the tibia. Where only a portion of a joint is damaged, a partial joint arthroplasty can be performed. In this procedure, one or more artificial implants replace only a portion of a joint. For example, where only one femoral or tibial condyle of the knee joint has been injured, only one of the injured lateral or medial femoral condyles is resected. The corresponding one of the lateral or medial tibial condyles is also resected. Implants replacing only a single condyle, referred to as uni-condylar implants, are mounted on the resected area of the femur and tibia.

Although joint replacement is now a common procedure that has met with popular success, conventional implants and related mounting techniques have significant shortcomings. For example, one problem with conventional joint implants and related techniques for mounting is that it can be difficult to fit, adjust, and/or exchange different implants during the fitting stage. That is, implants come in a variety of different sizes, shapes, and configurations. During the joint replacement procedure, the surgeon may often test a variety of different sized implants to determine the best fit and alignment. As conventional implants are screwed into or pounded onto the bone during placement, the fitting, adjustment, and/or replacement of different conventional implants can be difficult and potentially damaging to the bone.

Another shortcoming with current implants is an inability to easily replace the implant once the implant has been installed. For example, as mentioned above, a partial joint arthroplasty may be required, and a uni-condylar implant installed. Months or years later, the rest of the joint may deteriorate and the uni-condylar implant must be replaced with a total condylar implant. This occurs frequently with the knee. Using current prostheses and methods, replacing a uni-condylar implant with a total condylar implant requires removing the entire uni-condylar implant from the bone (including the anchoring system), drilling or otherwise creating a new hole in the bone to anchor the total joint implant, then installing the total joint implant with a new anchor. Because a new anchoring hole and anchor are required, more bone must be drilled into or otherwise removed, causing more pain for the patient, an increased possibility of infection, a longer recovery time, and generally more risk.

Accordingly, what is needed are implants and related methods for mounting the implants on an articular surface of a joint which enable easier fitting, alignment, testing, and/or replacement of implants. What is also needed are implants and related methods which enable easy replacement of uni-condylar implants with total condylar implants.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to implants for mounting at an articulation surface of an orthopedic joint and related methods. As used in the specification and appended claims, the terms "articulation surface" and "natural articulation surface" are broadly intended to include all natural articular surfaces of a bone forming a portion of an orthopedic joint and all articulation wear surfaces of a bone forming a portion of an orthopedic joint which are produced as a result of wear, trauma, disease, or other causes which remove all or a portion of the natural articular surface.

It is appreciated that the implants and methods of the present invention can be used for mounting an implant on virtually any articulation surface of any orthopedic joint in a human or other mammal. By way of example and not by limitation, the implants and methods of the present invention can be used in association with resurfacing an articulation surface of a knee joint, ankle joint, hip joint, shoulder joint, elbow joint, wrist joint, interphalangeal joint, or other joints. As such, the implants can be mounted on the proximal end and distal end of the femur, tibia, humerus, radius, and ulna, and on the articular surfaces of the scapula, pelvis, bones within the foot and hand, and other bone articular surfaces. Likewise, the implants and methods of the present invention can be used in facilitating a partial joint arthroplasty or a total joint arthroplasty.

In one embodiment of the present invention, the implants and/or methods are designed to be modular such that either the articulation bearing surface of the implant can be positioned on the bone after an anchor is inserted into the bone or the anchor can be inserted into the bone after the articulation bearing surface of the implant has been positioned on the bone. This ability allows for greater ease in adjustment and fitting of the implant at the time of initial placement and for greater ease in replacement of the implant.

Set forth below are several embodiments of the present invention used in association with replacing one or both condyles at the proximal end of a tibia. Alternative embodiments used with a femur and a hip are also set forth. It is again noted that these embodiments are only given by way of example and that one skilled in the art based on the teachings provided herein would be able to use corresponding implants and methods to prepare and/or mount an implant on other joint articulation surfaces.

Figure 1:
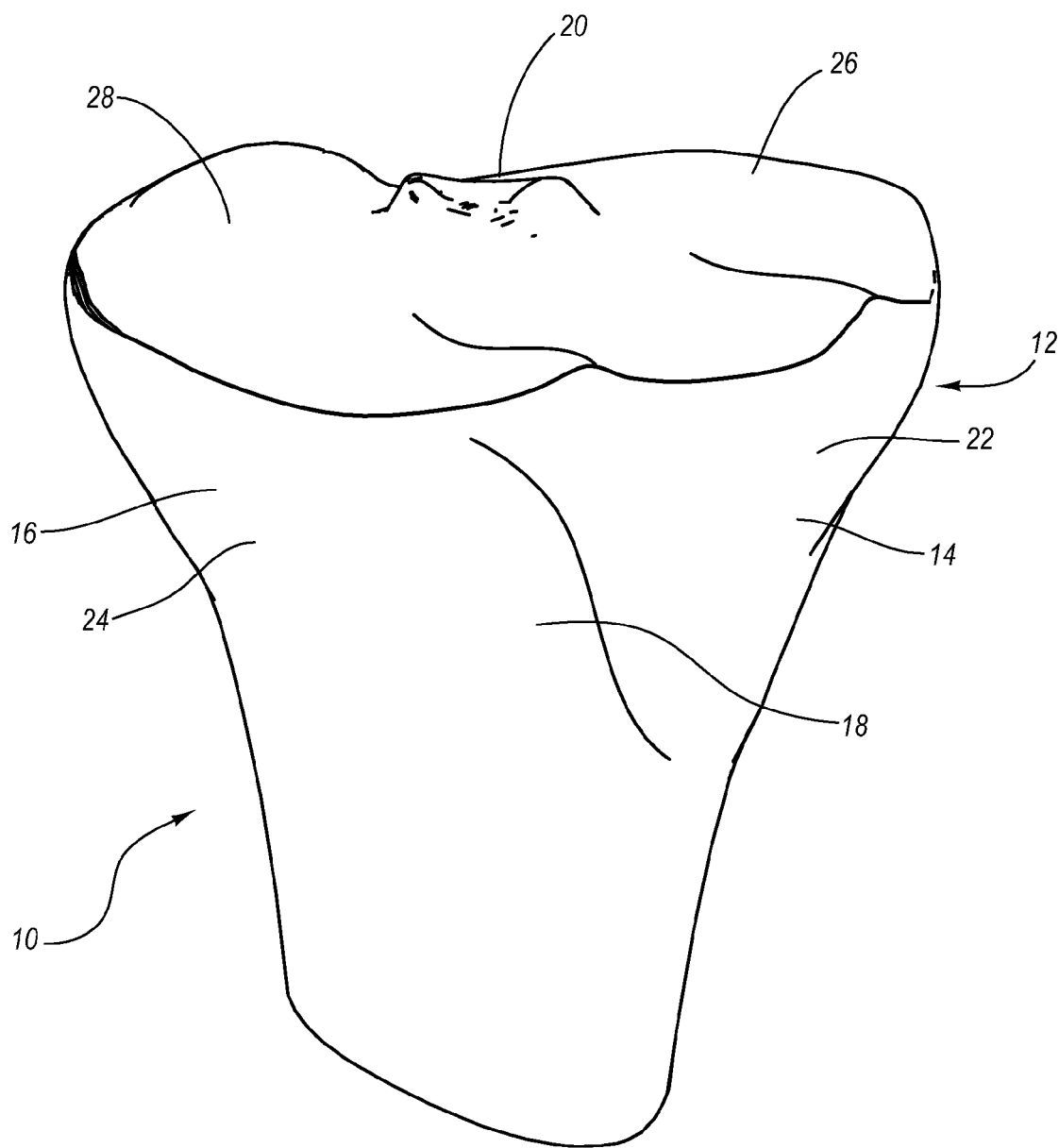
FIG. 1 is a perspective view of the proximal end of a tibia.

Depicted in FIG. 1 is a proximal end 10 of a tibia 12. Proximal end 10 has a lateral side 14 and a medial side 16 which each extend between an anterior side 18 and a posterior side 20. Proximal end 10 further comprises a lateral condyle 22 and a medial condyle 24. Lateral condyle 22 terminates proximally at a lateral facet 26 of a superior articular surface of tibia 12 while medial condyle 24 terminates proximally at medial facet 28 of a superior articular surface of tibia 12.

Although tibia 12 shown in FIG. 1 corresponds to a left leg, it is appreciated that the tibia of the right leg has a complimentary configuration and that the methods and apparatus of this specific example are equally applicable thereto. Thus, while reference is made to "medial" and "lateral" objects or directions, it is appreciated that these references would be reversed when using embodiments of the current invention with the right leg.

Figure 2:
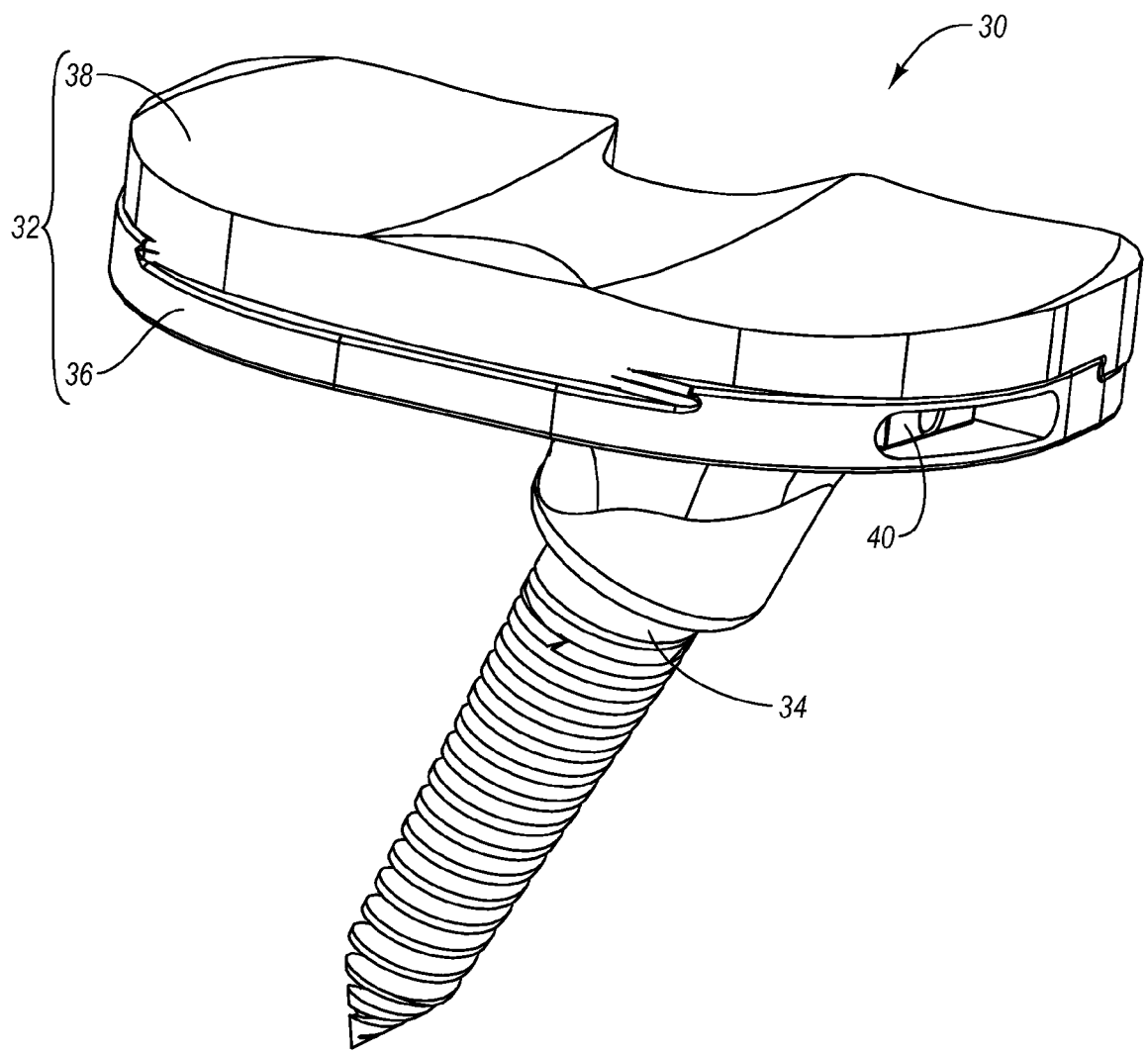
FIG. 2 is a perspective view of a total condylar implant according to one embodiment of the present invention that can be placed on the proximal end of the tibia shown in FIG. 1.
Figure 3:
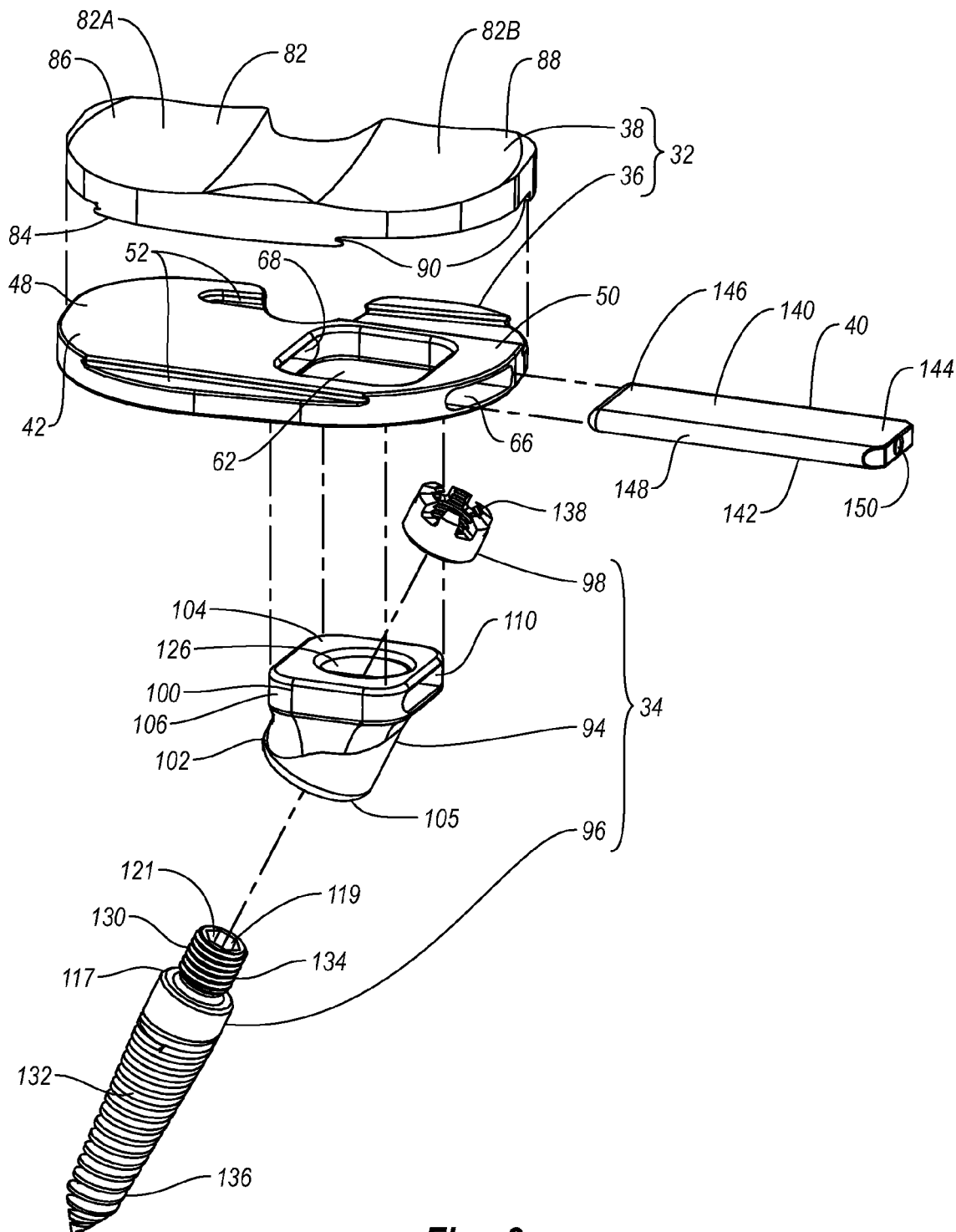
FIG. 3 is an exploded perspective view of the implant shown in FIG. 2.

Depicted in FIG. 2 is one embodiment of an inventive implant 30 incorporating features of the present invention that is designed for mounting on tibia 12. In general, implant 30 comprises a bearing assembly 32 attached to an anchor 34 that is adapted for mounting into a bone. More specifically, as depicted in FIG. 3, bearing assembly 32 comprises a tray 36 with a bearing member 38 adapted for mounting thereon. Anchor 34 projects down from tray 36, and means for securing tray 36 to anchor 34 are provided. In the depicted embodiment, the means for securing comprises a fastener 40. These elements, including alternative means for securing, are discussed in more detail below.

Figure 4:
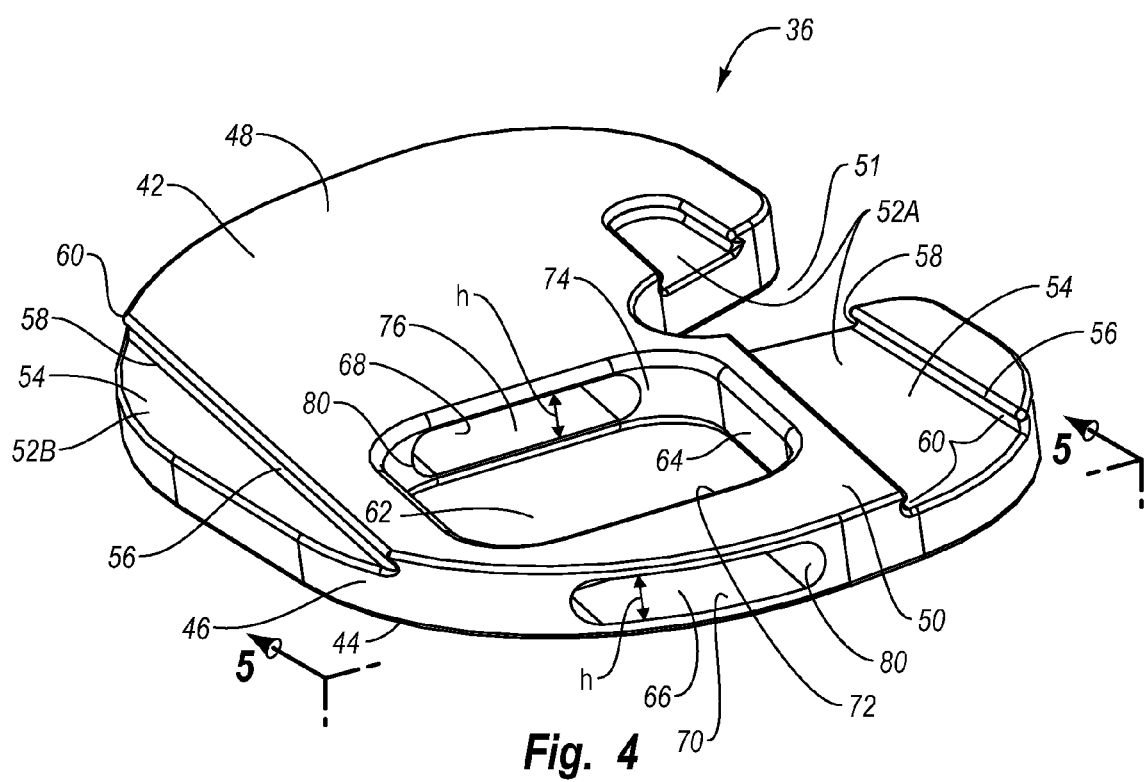
FIG. 4 is a top perspective view of the tray of the implant shown in FIG. 3.

As depicted in FIG. 4, tray 36 has a top surface 42 and an opposing bone apposition surface 44 with a perimeter edge 46 extending therebetween. Top surface 42 and bone apposition surface 44 are substantially flat and extend between a first end 48 and an opposing second end 50. A notch 51 extends between top surface 42 and bone apposition surface 44 and is formed on perimeter edge 46 at a substantially central location between opposing ends 48 and 50.

Top surface 42 is configured to receive bearing member 38. Specifically, in the depicted embodiment a first channel 52A and a second channel 52B are formed on top surface 42. First channel 52A is recessed on top surface 42 so as to extend from perimeter edge 46 at second end 50 to toward first end 48. Although not required, first channel 52A has a tapered, substantially V-shaped configuration. First channel 52A is bounded by a substantially flat floor 54 having a sidewall 56 upstanding therefrom. Sidewall 56 comprises a recess groove 58 which extends along floor 54 and an outwardly projecting lip 60 which projects along top surface 42. As such, the opposing sidewalls 56 of channel 52A form a mortise or guide to receive and secure a key projecting down from bearing member 38 as will be discussed below in greater detail.

Second channel 52B is spaced apart from first channel 52A but also extends from second end 50 to toward first end 48 of tray 36. In contrast to first channel 52A, however, second channel 52B continuously extends along perimeter edge 46. Common elements between channels 52A and 52B are identified by like reference characters. In alternative embodiments, it is appreciated that tray 36 can be formed with only one channel or three or more channels. Furthermore, the size, position, and configuration of the various channels can be varied. For example, second channel 52B can have the same configuration as first channel 52A. The general concept is that the channels are configured to that they can receivably engage bearing member 38. In this regard, side wall 56 can also have a variety of different configurations.

As will be discussed below in greater detail, during typical use of implant 30, proximal end 10 of tibia 12 (FIG. 1) is resected to form a tibial plateau. Bone apposition surface 44 of tray 36 is configured to sit on the tibial plateau and typically has a configuration complementary thereto. In this regard, bone apposition surface 44 can be substantially flat or can be curved such as having a convex curvature or concave curvature. Likewise, grooves can be formed on bone apposition surface 44 and/or projections can be formed extending from bone apposition surface 44. The projections can comprise fins, sharpened spikes, or the like. Such projections can be configured to penetrate into the bone or to be received within slots formed on the tibial plateau. The projections can also serve to strengthen tray 36 by increasing the bending moment of inertia of tray 36. It is also appreciated that one or more pockets can be formed on bone apposition surface 44 in which a porous bone ingrowth material can be disposed.

Tray 36 also bounds an opening 62 which extends completely through tray 36 between top surface 42 and bone apposition surface 44. Opening 62 is bounded by a sidewall 64 extending between top surface 42 and bone apposition surface 44. In the depicted embodiment opening 62 is large enough for all of anchor 34 to completely pass through opening 62. Although opening 62 is depicted as generally rectangular in shape, other shapes may alternatively be used, so long as opening 62 allows anchor 34 to be received into opening 62, as discussed below. By way of example and not limitation, opening 62 can be generally circular, oval, polygonal, irregular or any other shape. In the depicted embodiment opening 62 is shown being disposed at or toward second end 50 of tray 36. However, it is appreciated that opening 62 can alternatively be placed at or toward first end 48 or at other locations.

Figure 5:
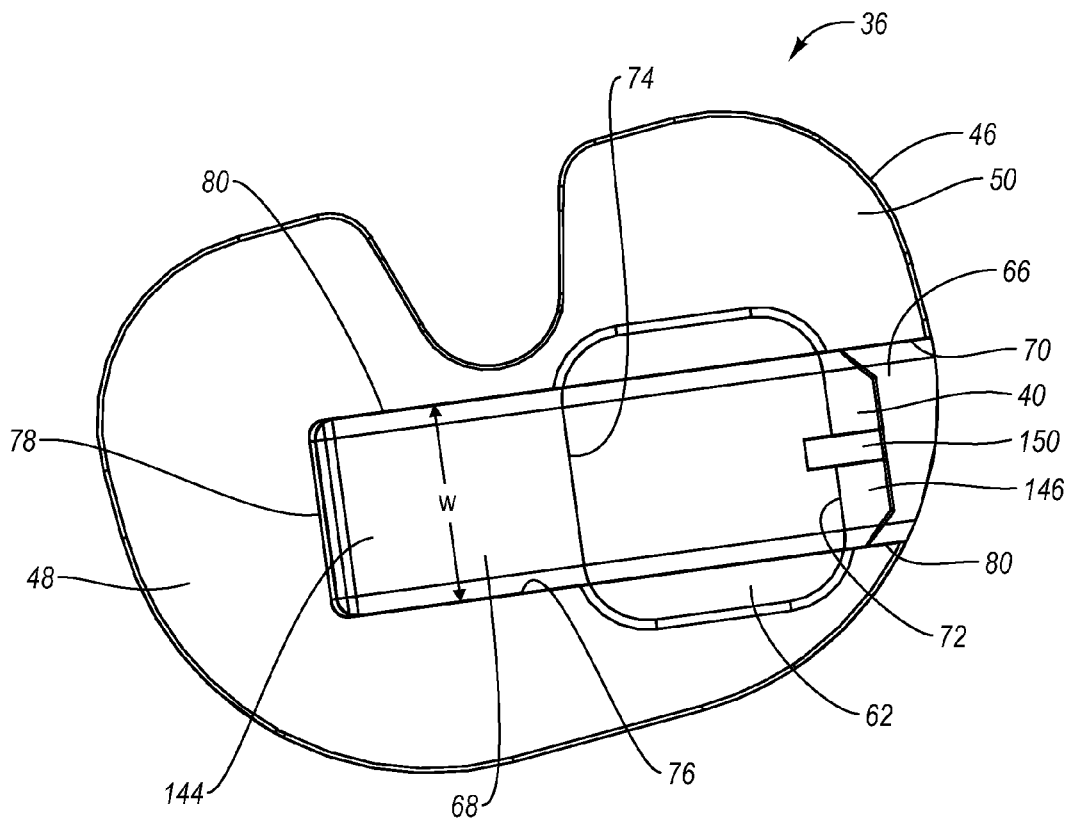
FIG. 5 is a cross-sectional top view of the tray shown in FIG. 4, with a fastener inserted therein.

Turning to FIG. 5 in conjunction with FIG. 4, a first passageway 66 and a second passageway 68 are horizontally formed in tray 36 so as to communicate with opening 62. Passageways 66 and 68 are formed to receive and secure the means for securing tray 36 to anchor 34. One embodiment of such means comprises fastener 40 as depicted in FIG. 5. Alternative means for securing are discussed below. First passageway 66 is bounded by an internal surface 70 that extends between perimeter edge 46 at the second end 50 of tray 36 to a sidewall 72 of opening 62. As a result, first passageway 66 forms a tunnel that is open at opposing ends. Second passageway 68 is bounded by an internal surface 76 and extends a distance from a medial sidewall 74 of opening 62 to toward first end 48 of tray 36. Second passageway 68 terminates at a closed distal end 78. Although depicted as terminating within tray 36, it is appreciated that second passageway 68 may alternatively extend to perimeter edge 46 at the first end 48 of tray 36.

First and second passageways 66 and 68 have a height h and width w that are substantially constant along the entire length of both passageways. In the depicted embodiment, passageways 66 and 68 are shaped as slots with rounded side surfaces 80. In other embodiments, side surfaces 80 are alternatively shaped, such as being squared off, trapezoidal or the like. First and second passageways 66 and 68 are longitudinally and vertically aligned to be able to receive fastener 40 when fastener 40 is inserted into tray 36 through first passageway 66, as shown in FIG. 5.

Although first and second passageways 66 and 68 are depicted as slots, it is appreciated that other passageway shapes may alternatively be employed in other embodiments depending on the means provided for locking tray 36 to anchor 34. By way of example and not limitation, first and second passageways 66 and 68 can be round, oval or rectangular when viewed transversally. First and second passageways 66 and 68 can have internal surfaces 70 that are smooth or threaded. Although depicted as being disposed on the second end 50 of tray 36, it is also appreciated that first and second passageways 66 and 68 can be disposed on the first end 48 of tray 36 if opening 62 is formed on the first end 48 of tray 36. First and second passageways 66 and 68 can also be tapered to allow for a greater press-fit connection with fastener 40. In any event, first and second passageways 66 and 68 are shaped to be able to receive the means for securing tray 36 to anchor 34.

Figure 6:
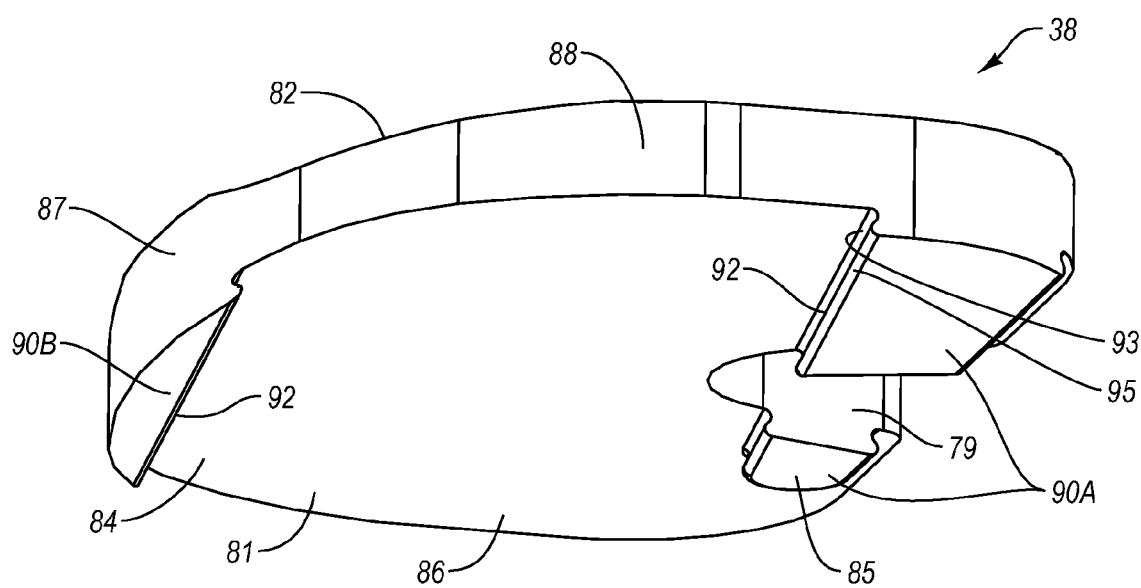
FIG. 6 is a bottom perspective view of the bearing member of the implant shown in FIG. 3.

With reference to FIGS. 2 and 6, bearing member 38 comprises a top articular surface 82 and a bottom surface 84 which each extend between a first end 86 and an opposing second end 88. A perimeter edge 87 extends between top articular surface 82 and bottom surface 84 with a notch 79 being formed thereon. Top surface 82 is configured to interact with a femoral component. In the depicted embodiment top surface 82 has a pair of spaced apart concave pockets 83A and 83B that are each adapted to receive a condyle from a femoral component. In alternative embodiments it is appreciated that top surface 82 can have a variety of different configurations depending on the design for the corresponding implant that is to interact with top surface 82.

Bottom surface 84 of bearing member 38 has a configuration substantially complementary to top surface 42 of tray 36. Specifically, bottom surface 84 includes a substantially flat floor 81 having a pair of elongated keys 90A and 90B projecting therefrom. Key 90A has a configuration substantially complementary to channel 52A (FIG. 4) of tray 36 and includes a sidewall 92 extending from floor 81 to an end face 85. Sidewall 92 has a recessed groove 93 extending along floor 81 and an outwardly projecting lip 95 extending along end face 85. Sidewall 92 of key 90A is substantially complementary to sidewall 56 of channel 52A such that key 90A forms a tenon that can slide into channel 52A to form a secure, releasable connection therewith. An elongated second key 90B also projects from floor 81 and has a sidewall 92. Key 90B is configured to slide into channel 52B of tray 36 and engage with sidewall 56 thereof, thereby further securing bearing member 38 to tray 36. Alternative embodiments as discussed with tray 36 are also applicable to bearing member 38.

Channels 52A and B and keys 90A and B are one embodiment of means for connecting bearing member 38 to tray 36. In alternative embodiments, different techniques such as snap fit, press fit, or mechanical connector can be used to secure bearing member 38 and tray 36 together. Bearing member 38 may be of any suitable biocompatible material. Typically, bearing member 38 is comprised of a polymeric material although composites, metals, and other materials can also be used.

Figure 7:
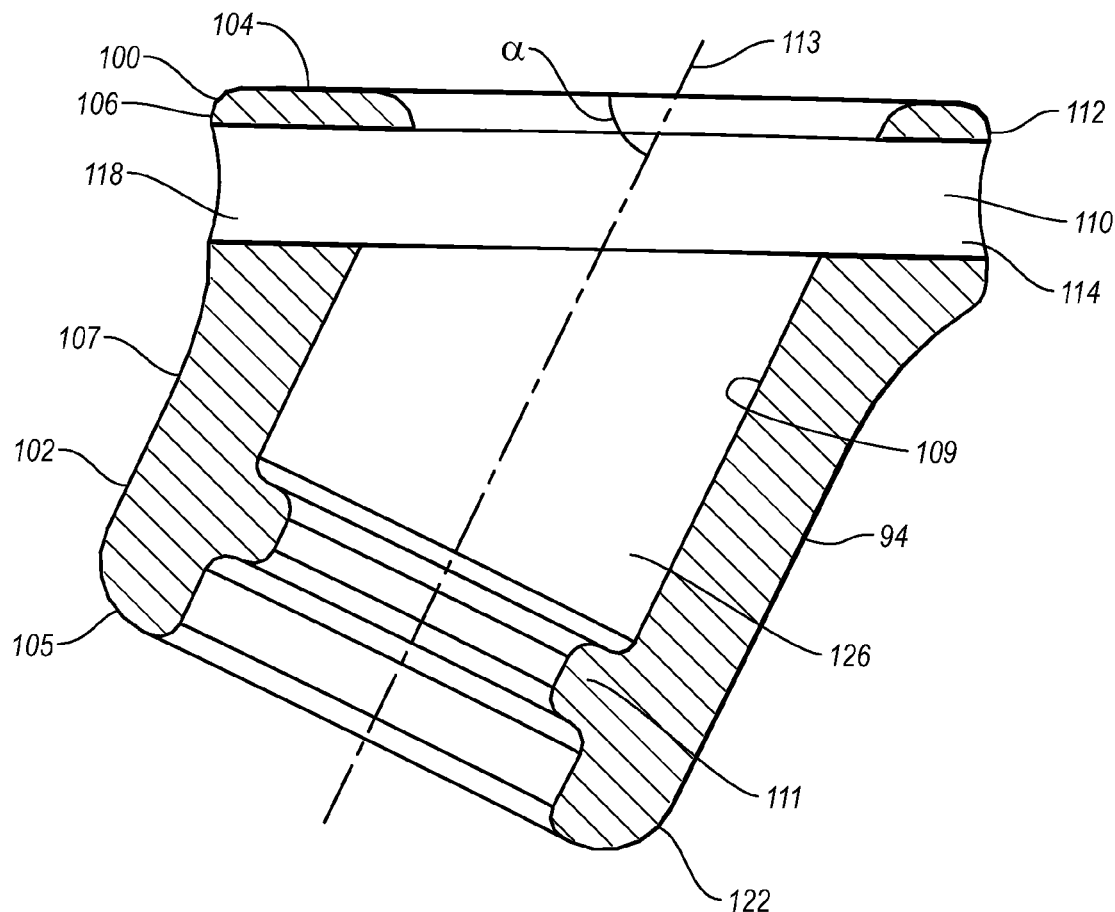
FIG. 7 is a cross sectional side view of the keel shown in FIG. 3.

Returning to FIG. 3, anchor 34 comprises a keel 94 with a stem 96 that projects downward therefrom. A locking nut 98 is used to secure stem 96 to keel 94. Anchor 34 is used to secure implant 30 to proximal end 10 of tibia 12. In general, keel 94 comprises an upper portion 100 that terminates at a top surface 104 and a lower portion 102 that terminates at a bottom surface 105. As depicted in FIG. 7, keel 94 also has an interior surface 109 that bounds a bore 126 extending through keel 94 between top surface 104 and bottom surface 105. Radially inwardly projecting from interior surface 109 at a location toward bottom surface 105 is an annular flange 111. Flange 111 forms a seat against which locking nut 98 can bias.

Returning to FIG. 3, upper portion 100 is used to mount and secure keel 94 to tray 36 while lower portion 102 is used to mount and secure keel 94 to stem 96. As shown in the depicted embodiment, upper and lower portions 100 and 102 are integrally formed. In other embodiments upper and lower portions 100 and 102 can be separate and discrete components that are connected together. Upper portion 100 is configured to fit within opening 62 in tray 36 and can selectively pass therethrough if desired. Upper portion 100 is shown having a transverse cross section that is substantially complementary to the transverse cross section of opening 62. That is, upper portion 100 is rectangularly shaped when viewed perpendicularly to top surface 104 so as to substantially match the shape of opening 62. Alternative cross sectional shapes can also be used so as to match alternative shapes for openings 62 of tray 36. Top surface 104 of upper portion 100 is substantially planar so that it can sit flush with top surface 42 of tray 36. In addition, upper portion 100 has a sidewall 106 that is substantially the same thickness as tray 36 at opening 62.

A third passageway 110 transversely extends all the way through upper portion 100 of keel 94 so as to intersect with bore 126. As depicted in FIG. 7, third passageway 110 is bounded by an internal surface 112 and extends from a first opening 114 on sidewall 106 of keel 94 to a second opening 118 on the opposing side of keel 94. Third passageway 110 is sized and shaped to substantially align with first and second passageways 66 and 68 of tray 36 when upper portion 100 of keel 94 is received within opening 62 of tray 36. Aligned passageways 66, 68, and 110 combine to form a contiguous passageway which can receive fastener 40. Thus, third passageway 110 has substantially the same height h and width w as first and second passageways 66 and 68.

Third passageway 110 is depicted as a slot with rounded side surfaces to match first and second passageways 66 and 68. It is appreciated that other passageway shapes may alternatively be employed in third passageway in other embodiments to match alternatively shaped first and second passageways 66 and 68. By way of example and not limitation, third passageway 110 can be substantially round, oval or rectangular when viewed transversally. Third passageway 110 can have walls that are smooth or threaded to match first and second passageways 66 and 68.

As mentioned above, lower portion 102 of keel 94 is used to mount and secure keel 94 to stem 96. Lower portion 102 angles down from upper portion 100. Lower portion 102 is substantially rectangular where it connects to upper portion 100 and transitions to being substantially cylindrical in shape at a bottom end 122. A central longitudinal axis 113 extends through lower portion 102 and the portion of bore 126 disposed therein. In one embodiment, lower portion 102 is formed so that an inside angle α is formed between top surface 104 of keel 94 and longitudinal axis 113 that is less than 80° and more commonly less than 70° or 60°. However, in other alternative embodiments, lower portion 102 and bore 126 can be positioned so that the angle α is 90°.

Returning to FIG. 3, stem 96 is an elongated member having a proximal end 134 and an opposing distal end 136. Stem 96 includes a head 130 formed at proximal end 134 and a shank 132 projecting from head 130. Shank 132 tapers to a point at distal end 136 and has threads formed thereon so that shank 132 can be threaded or screwed into tibia 12 so as to securely engage tibia 12. At the intersection between head 130 and shank 132, shank 132 has a larger outer diameter than head 130 so that an annular shoulder 117 is formed thereat. Head 130 is threaded so as to enable locking nut 98 to be screwed thereon, as described below.

In one embodiment of the present invention, means are provided for coupling a driver to proximal end 134 of stem 96. By way of example and not by limitation, proximal end 134 terminates at a terminal end face 119 in which a socket 121 is formed. Socket 121 is non-circular to that a driver (not shown) can be received within socket 121 and then rotated so as to rotate stem 96. In the embodiment depicted socket 121 has a polygonal configuration although other non-circular shapes can also be used. In other alternative embodiments, a stem having a polygonal or other non-circular transverse cross section can project from end face 119 for engaging with a driver. In still other embodiments, slots or other structures can be formed on end face 119 for engaging with a driver.

Locking nut 98 comprises a nut with internal threads that match the threads of head 130 of stem 96, thus allowing locking nut 98 to be able to be screwed onto head 130. One embodiment of the present invention also includes means for coupling a driver to locking nut 98. By way of example and not by limitation, locking nut 98 has a plurality of cut-outs or ridges 138 formed on a proximal end thereof to allow nut 98 to be manually screwed onto head 130 by using a tool with matching cut-outs or ridges that engage with cut-outs or ridges 138. It is appreciated that a variety of different structures can be formed on nut 98 to engage with a driver. For example, the exterior surface of nut 98 can have a polygonal configuration to match with a driver.

Figure 8:
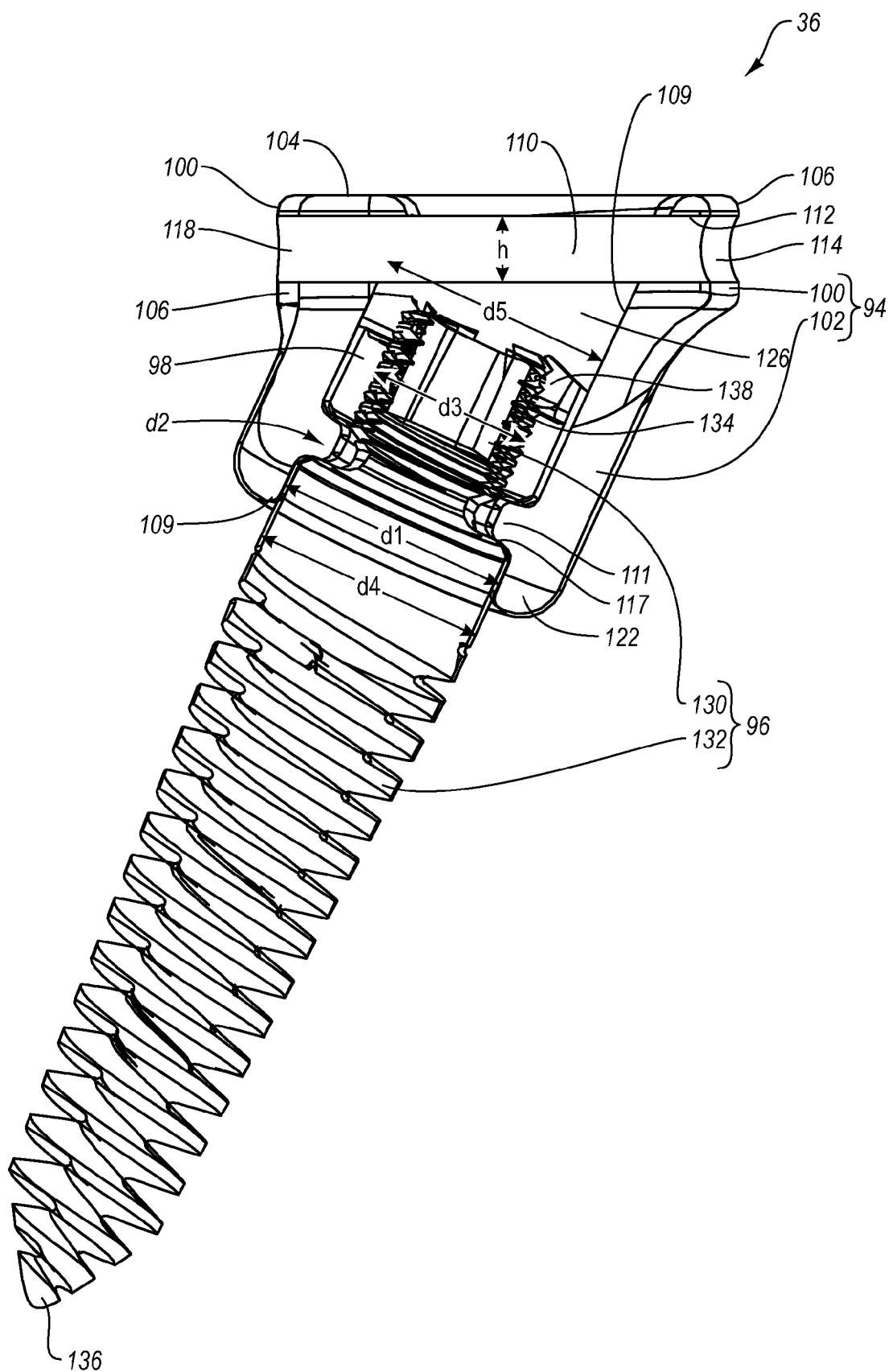
FIG. 8 is a cross-sectional side view of an anchor used in the implant shown in FIG. 3.

Turning to FIG. 8, head 130 of stem 96 has an outer diameter d3 that is less than inner diameter d2 of annular flange 111 of keel 94 such that head 130 can fit through annular flange 111 while shoulder 117 of stem 96 biases against flange 111. Locking nut 98 has an outer diameter d5 that is smaller than the diameter d1 of bore 126 but greater than the inner diameter d2 of annular flange 111 so that locking nut 98 can be screwed onto threaded head 130 and biased against annular flange 111, thereby securely connecting stem 96 to keel 94.

Returning to FIG. 5 in conjunction with FIG. 3, means are provided for locking tray 36 to anchor 34. The means can be permanent, releasable, or removable. By way of example and not by limitation, in the depicted embodiment means for securing comprises fastener 40. Fastener 40 includes generally planar top and bottom surfaces 140 and 142 extending between a proximal end 144 and a spaced-apart distal end 146. A perimeter sidewall 148 extends between top surface 140 and bottom surface 142. Fastener 40 has a height and width that are equal to or slightly less than the height and width, respectively, of passageways 66, 68, and 110 such that when distal end 146 of fastener 40 is inserted into first passageway 66 and pushed toward the first end 48 of tray 36, fastener 40 passes through first passageway 66, third passageway 110 of keel 94 (if keel 94 is inserted into opening 62), and into second passageway 68, establishing a snug, press-fit connection.

Although the fastener 40 is described above as having a uniform height and width along the length of fastener 40, it is appreciated that in some embodiments top surface 140 and bottom surface 142 lie in diverging planes resulting in fastener 40 being tapered along the length thereof. Similarly, in some embodiments, the width of fastener 40 is tapered toward the distal end 146 of fastener 40. Tapering of fastener 40 aids in insertion of fastener 40 while increasing the frictional engagement between the various parts.

A threaded bore 150 is formed in sidewall 148 at the proximal end 144 of fastener 40 to aid in the insertion and extraction of fastener 40. That is, an insertion/extraction tool (not shown) with a corresponding threaded end can be screwed into bore 150 to aid in the insertion and/or extraction of fastener 40 into or out of tray 36 and keel 34.

Other means for securing keel 34 to tray 36 can also be used. For example, instead of being generally flat and thin, fastener 40 can be generally round, oval or rectangular when viewed transversally. In other alternative embodiments, a threaded fastener, such as a bolt or screw, can be passed through tray 36 and keel 34 so as to secure the members together. In one alternative, it is appreciated that the fastener need not extend all the way through keel 94 but can terminate therein. As such, second passageway 68 can be eliminated. Furthermore, wide fastener 40 can be replaced with two or more narrower fasteners, such as in the form of elongated pins, that each separately extend through tray 36 and keel 34. In other embodiments, still other types of fasteners can be used such as clips, clamps, expansion bolts, and the like. Of course, the size and shape of first and second passageways 66 and 68 of tray 36 and third passageway 110 of keel 94 must be adapted to receive the type of means used for locking.

As mentioned above, bearing member 38 is typically formed from a polymeric biocompatible material. While the other components of implant 30 are also made from a biocompatible material, they are typically made from a metal such as titanium, titanium alloy, or stainless steel. Other materials, such as ceramics, composites, plastics or the like, can also be used.

Figure 9:
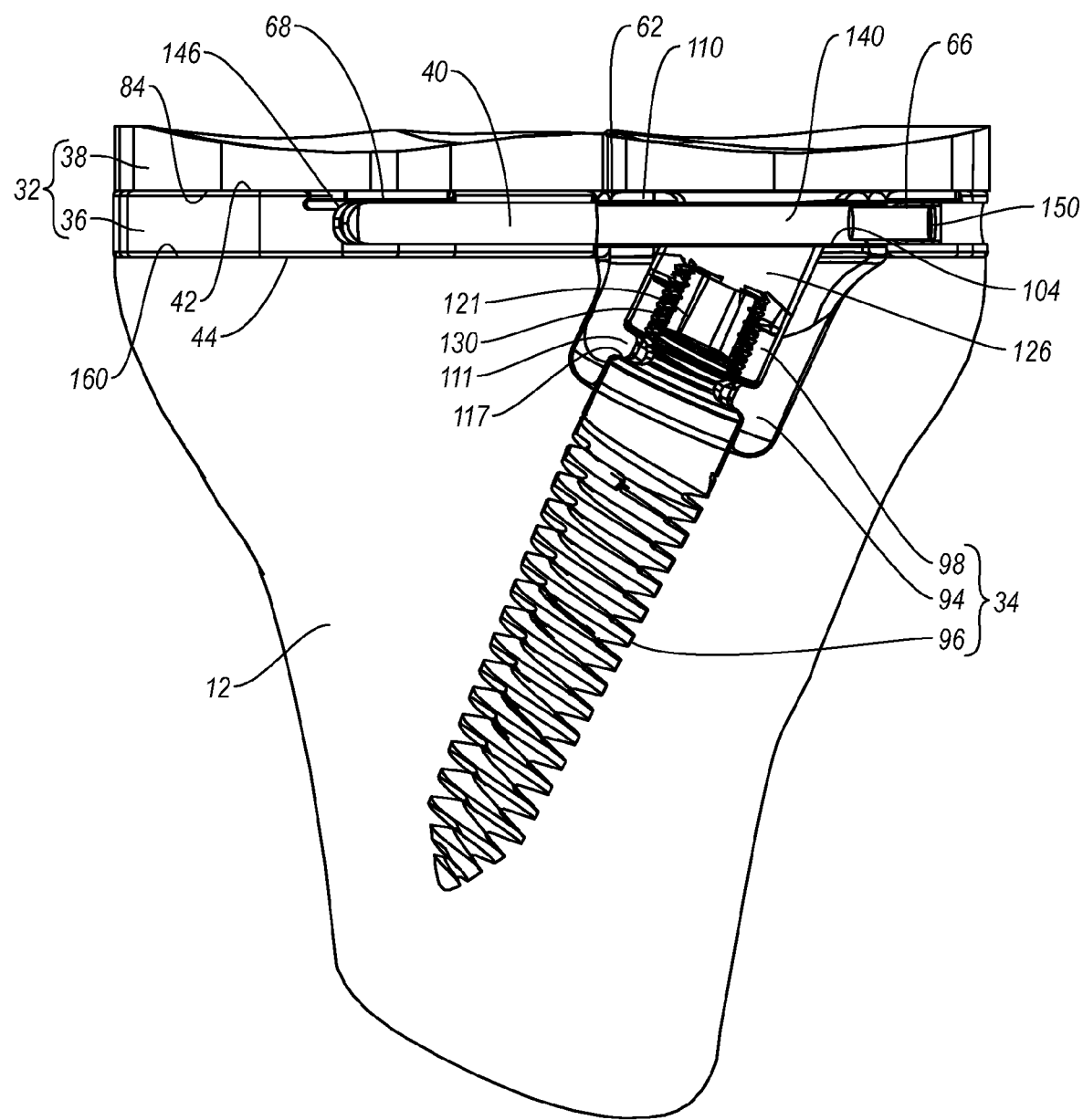
FIG. 9 is a cross sectional side view of the implant shown in FIG. 2 mounted on the tibia shown in FIG. 1.

Turning to FIG. 9 in conjunction with FIG. 3, one method of assembly and implantation of implant 30 on tibia 12 will not be described. As with any joint arthroplasty, the articulation surface of the bone must be prepared before an articular implant can be mounted thereon. In a total knee arthroplasty of the present invention the proximal end of tibia 12 is transversely resected so as to remove the tibial condyles and form a substantially flat tibial plateau 160. Once tibia plateau 160 has been prepared, stem 96 is screwed or otherwise secured into tibia plateau 160 at the proximal end of the tibia 12. This is typically accomplished by predrilling or reaming a hole on tibia plateau 160 and then screwing stem 96 into the hole. The predrilled hole is formed at an orientation complementary to the angle orientation of keel 94. A driver is coupled with socket 121 to assist in mounting stem 96.

Once stem 96 is secured in tibia 12 at the desired location and orientation, keel 94 is placed over the top of stem 96 such that head 130 is received into bore 126. Head 130 is passed through flange 111 so that shoulder 117 biases against flange 111. Locking nut 98 is then inserted into bore 126 from top surface 104 of keel 94, and securely screwed onto threaded head 130 using a driver as previously discussed. When tightened on threaded head 130, locking nut 98 biases against the opposing side of annular flange 111, thereby rigidly connecting keel 94 to stem 96 and preventing keel 94 from moving with respect to stem 96. At this point, anchor 34, consisting of keel 94 and stem 96 rigidly connected by locking nut 98, is secured to tibia 12.

Next, tray 36 is placed on the proximal end of tibia 12 and secured to anchor 34. In the depicted embodiment, this is accomplished by placing tray 36 on top of anchor 34 such that upper portion 100 of keel 94 is received into opening 62 of tray 36. The positioning is made so that first and second passageways 66 and 68 of tray 36 are aligned with third passageway 110 in keel 94. In this position, bone apposition surface 44 of tray is sitting upon tibial plateau 160 of tibia 12. Here it is noted that care is taken to secure keel 94 in the proper orientation on stem 96 so that tray 36 is properly orientated on tibial plateau 160 when coupled with keel 94. If necessary, locking nut 98 can be loosened and the orientation of keel 98 adjusted without having to loosen or adjust stem 96.

Once first, second, and third passageways 66, 68 and 110 are aligned, the distal end 146 of fastener 40 is inserted into first passageway 66 at the second end 50 of tray 36. Fastener is then advanced into third passageway of keel 92 and second passageway of tray 36, thereby forming a press-fit connection between fastener 40 and the internal surfaces 70, 76, and 112 of passageways 66, 68, and 110, respectively. An insertion tool may be removably screwed into or otherwise attached to bore 150 in the proximal end 144 of fastener 40 to aid in the insertion of fastener 40, but this is not required. When fully inserted, fastener 40 is fully disposed within the combination of passageways 66, 68, and 110. This rigidly secures tray 36 to anchor 34. If an insertion tool was used to insert fastener 40, it is unscrewed or otherwise disconnected from bore 150 of fastener 40.

Finally, bearing member 38 is then secured to tray 36 to form bearing assembly 32. In the depicted embodiment, this is accomplished by biasing bottom surface 84 of bearing member 38 against top surface 42 of tray 36 and sliding bearing member 38 over tray 36 until keys 90A and B on the bottom surface 84 of bearing member 38 are snugly fit into channels 52A and B on top surface 42 of tray 36 (see FIGS. 4 and 6). Other methods known in the art alternatively can be used to secure bearing member 38 to tray 36 to form bearing assembly 32.

While the above steps provide one method for the assembly and installation of implant 30, it is appreciated that many of the steps may be performed in a different order than the order listed. For example, bearing member 38 can be secured to tray 36 before or after tray is mounted to anchor 34. In fact, in some embodiments bearing member 38 can be integrally or permanently mounted to tray 36.

In another alternative order of steps for installing implant 30, tray 36 can first be positioned on tibial plateau 160. After tray 36 is positioned, stem 96 can be passed through opening 62 in tray 36 and then advanced into tibial 12. Keel 94 is then passed into opening 62 of tray 36 and over head 130 of stem 96. Locking nut 98, as described above, is then used to secure keel 98 to stem 96. Fastener 40 is then used to rigidly secure tray 36 to anchor 34, as described above. Finally, bearing member 38 is mounted to tray 36.

Figure 10:
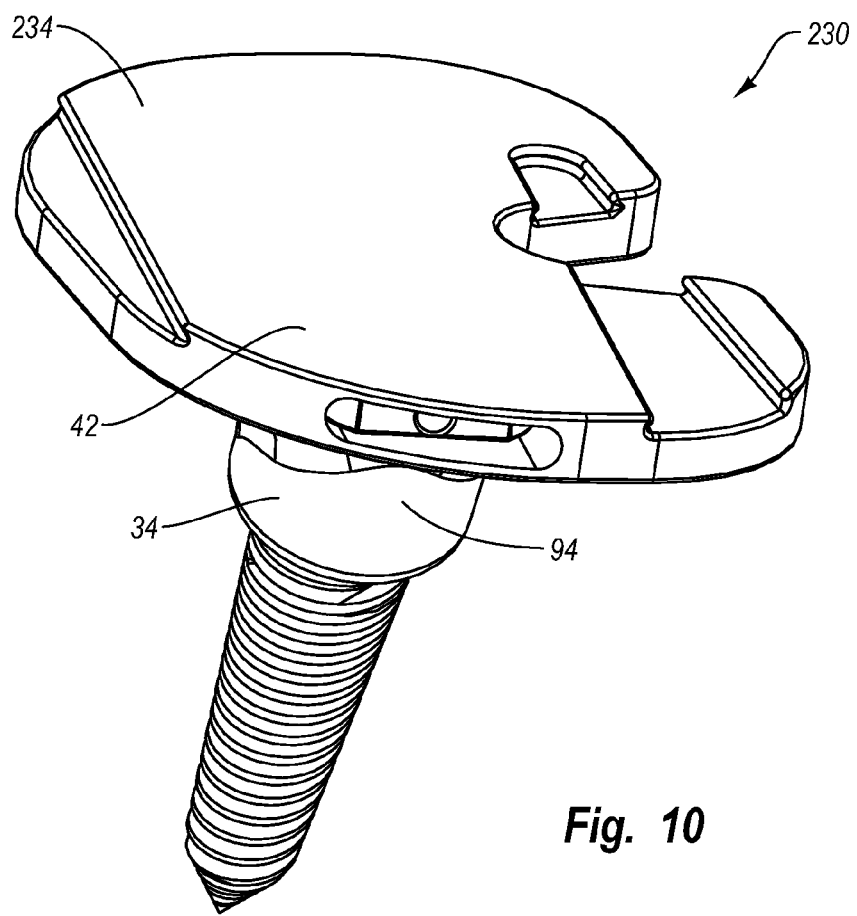
FIG. 10 is a perspective view of a total condylar implant (shown without a bearing member) according to an alternative embodiment of the present invention.
Figure 11:
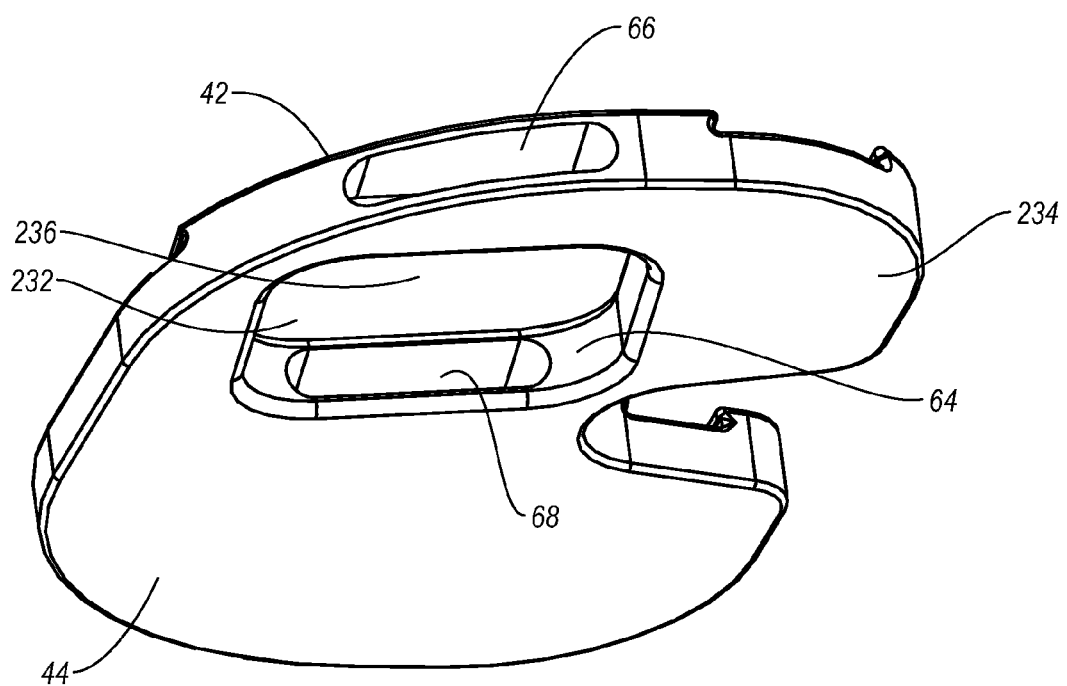
FIG. 11 is a bottom perspective view of a tray used in the implant shown in FIG. 10.

It is noted that where the first above discussed method of assembly is used, it is not necessary that opening 62 extend all the way through tray 36. Rather, opening 62 need only extend from bone apposition surface 44 to first passageway 66 and second passageway 68. For example, depicted in FIGS. 10 and 11 is an alternative embodiment of an inventive total condylar implant 230 (shown without bearing member 38) which incorporates features of the present invention. Like elements between implant 30 and implant 230 are identified by like reference characters.

Implants 30 and 230 are substantially similar except that as opposed to tray 36 having an opening 62 which extends completely through tray 36 between top surface 42 and bone apposition surface 44, the opening 232 in tray 234 does not extend through top surface 42. Opening 232 is formed on bone apposition surface 44 and is bounded by a substantially flat floor 236 having sidewall 64 extending therefrom. First passageway 66 and second passageway 68 communicate with opening 232. When anchor 34 is mounted to tray 234, keel 94 abuts floor 236. In addition to that previously discussed, however, having opening 62 extend all the way through tray 36 can provide added benefits. For example, having opening 62 extend through tray 36 enables tray 36 to be used as a template for the mounting of anchor 34 on tibial plateau 160 and can assist in making proper alignment with anchor 34.

Figure 12:
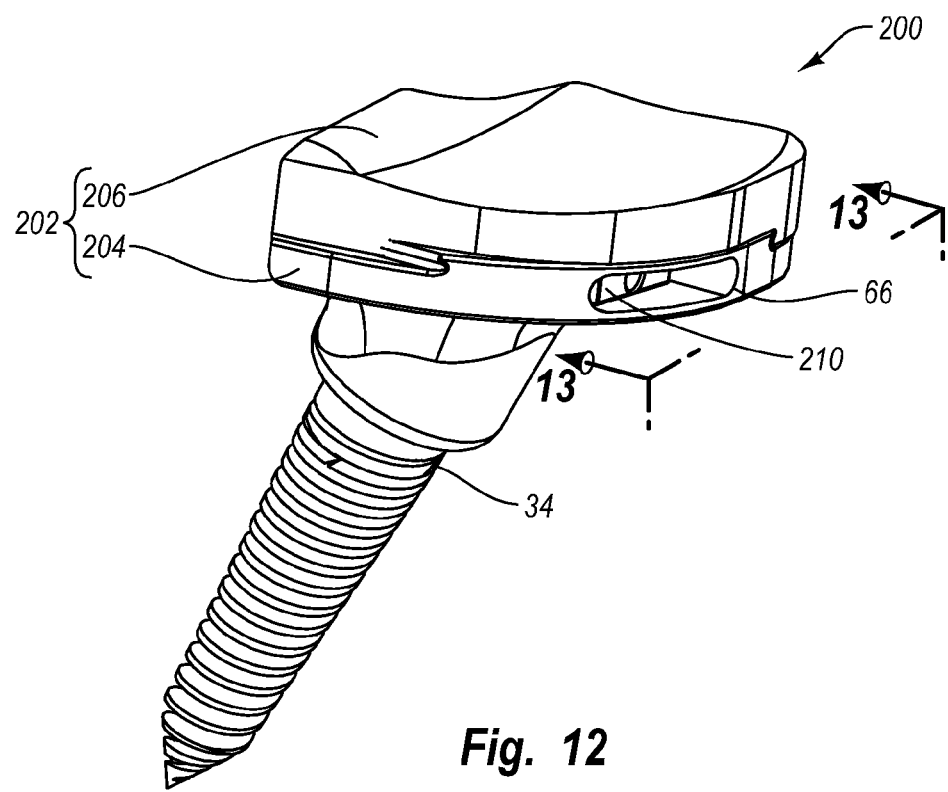
FIG. 12 is a perspective view of an uni-condylar implant according to one embodiment of the present invention that can be placed on the proximal end of the tibia shown in FIG. 1.
Figure 13:
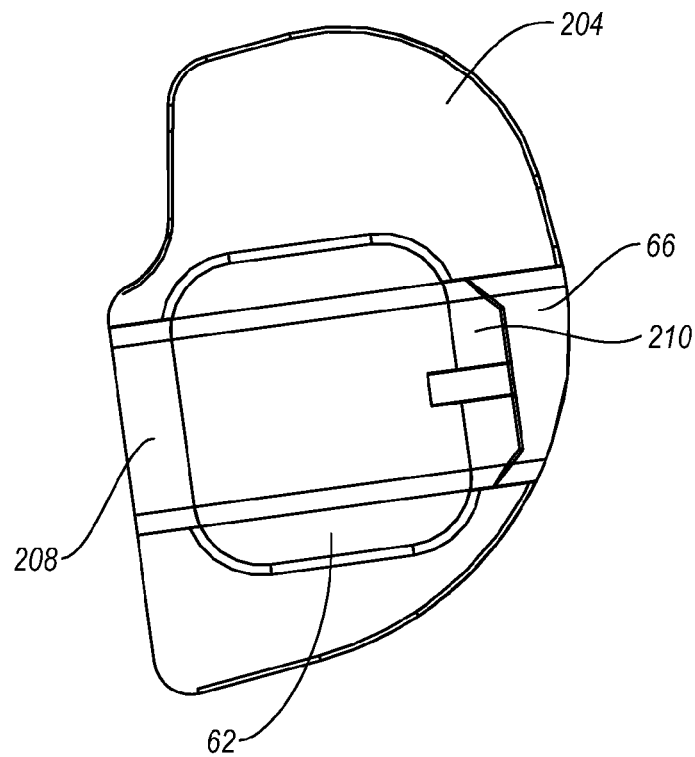
FIG. 13 is a cross-sectional top view of a tray used in the uni-condylar implant shown in FIG. 12.

Tray 36 and bearing member 38 as depicted and discussed above are designed for use with a total joint arthroplasty. That is, tray 36 and bearing member 38 form part of a total condylar implant. Alternative embodiments of the present invention, however, can also be used in partial joint arthroplasty. For example, depicted in FIGS. 12 and 13 is a uni-condylar implant 200 for replacing only a single condyle at the proximal end of tibia 12. Like elements between total condylar implant 30 and uni-condylar implant 200 are identified by like reference characters.

Implants 30 and 200 are substantially similar except that as opposed to bearing assembly 32, comprising tray 36 and bearing member 38, being sized to replace both the medial and lateral condyles at the proximal end of tibia 12, bearing assembly 202, comprising tray 204 and bearing member 206, is sized to replace only one of the condyles. Because of the smaller size of tray 204, second passageway 208 is shorter than second passageway 68 and fastener 210 is correspondingly shorter than fastener 40 so as to not protrude from first passageway 66 when fully inserted into second passageway 208. The same steps discussed above for mounting total condylar implant 30 can also be used for mounting uni-condylar implant 200. In mounting uni-condylar implant 200, however, only one of the condyles is resected from tibia 12.

Although not required, in the depicted embodiment opening 62 remains the same size for both trays and the same anchor 34 can be used with both implants 30 and 200. This allows uni-condylar implant 200 to be replaced with total condylar implant 30 using the same anchor 34. For example, initially it may only be necessary to mount a uni-condylar implant 200 where only one of the condyles of a knee joint has been damaged. After subsequent ware or damage to the knee joint, however, it may be necessary to replace uni-condylar implant 200 with total condylar implant 30.

To remove uni-condylar implant 200, bearing assembly 202 is simply disconnected from anchor 34. To accomplish this, the insertion tool is screwed into bore 150 on the proximal end 144 of fastener 40. Using the tool, fastener 40 is then completely retracted out of tray 204, thereby disengaging from passageways 66, 68, and 110. Once fastener 40 is removed, bearing assembly 202 is lifted off of anchor 34 and removed. Anchor 34, however, remains secured to tibia 12. After resecting the remaining condyle on tibia 12, total condylar bearing assembly 32 is then positioned on the proximal end of the tibia 12 and connected to anchor 34 using fastener 40 in the same manner as previously discussed.

As previously discussed and depicted, stem 96 of both implants 30 and 200 is typically sloped relative to corresponding tray 36, 204. By initially sloping stem 96 when mounting uni-condylar implant 200, stem 96 is more centrally mounted on tibia 12. As a result of this central mounting, the same stem 96 can also be used for mounting total condylar implant 30 without having to reset stem 96.

Figure 14:
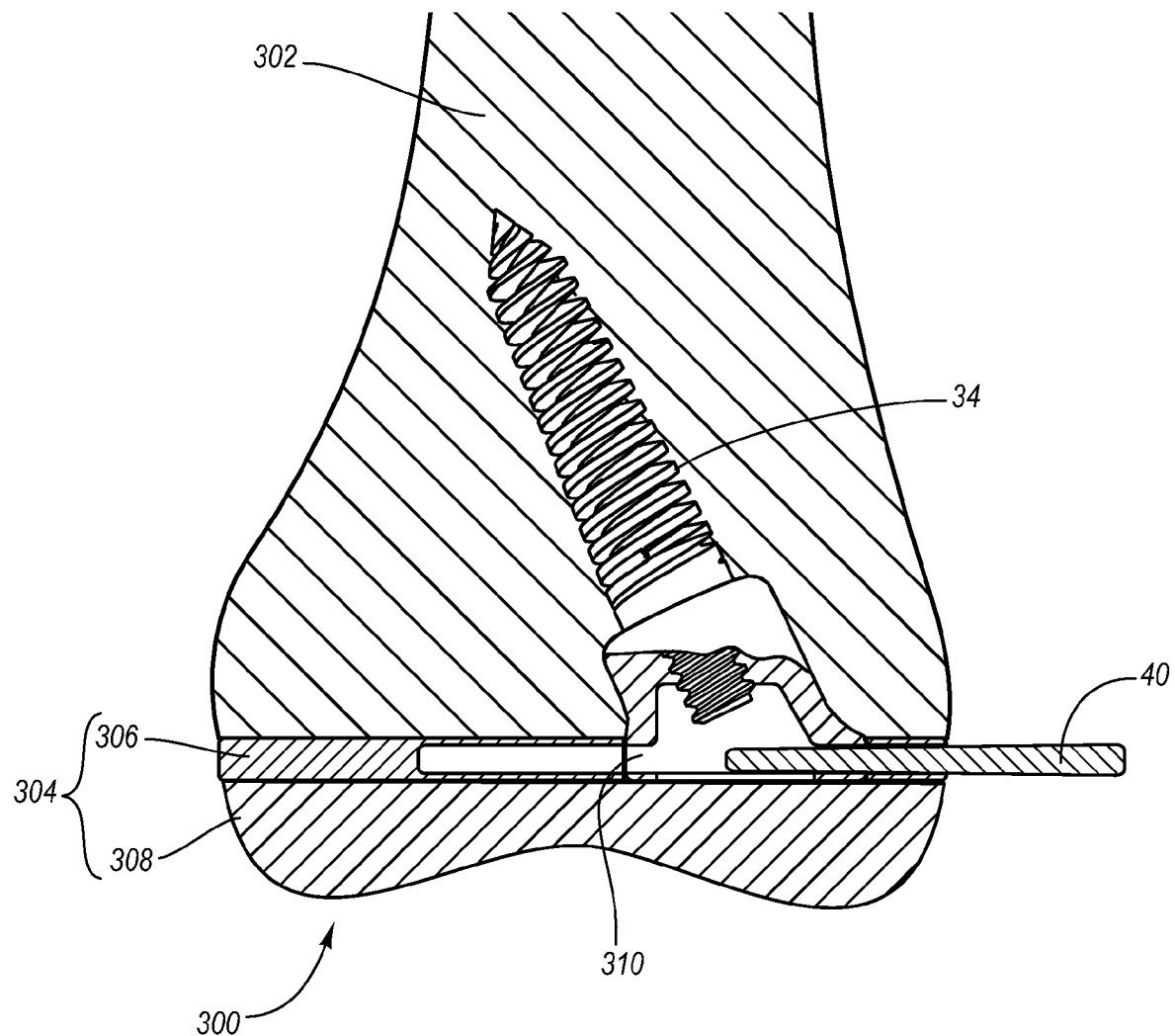
FIG. 14 is a cross-sectional side view of an alternative embodiment of an inventive implant mounted on the distal end of a femur with a fastener partially inserted.

As noted above, the present invention can also be used in association with replacing one or both condyles at the distal end of a femur. For example, depicted in FIG. 14 is a total condylar implant 300 for replacing both condyles at the distal end of a femur 302 which incorporates features of the present invention. Like elements between total condylar implant 30 and total condylar implant 300 are identified by like reference characters.

Implant 300 comprises a bearing assembly 304 attached to anchor 34 that is adapted for mounting into femur 302. Bearing assembly 304 comprises a tray 306 and a bearing member 308 adapted for mounting thereon. Bearing member 304 is configured to replace the condyles resected at the distal end of femur 302. Bearing member 308 can be mounted to tray 306 in various ways. For example, similar to previously described embodiments, bearing member 308 and tray 306 can have matching mortices and tenons formed thereon which secure bearing member 308 to tray 306. Other methods of mounting can alternatively be used, such as using adhesives, snap fit connections, or other methods known in the art. Alternatively, bearing member 308 and tray 306 can be integrally formed of the same material.

Anchor 34 projects away from tray 306, and is adapted to be inserted and secured in the distal end of femur 302. Fastener 40 secures tray 306 to anchor 34 in the same manner as described above with regard to tibial implant 30. Similar to tray 36, tray 306 also bounds an opening 310 which extends completely through tray 306 and is large enough for all of anchor 34 to completely pass through. Similar to previous embodiments of the current invention, once anchor 34 has been implanted and secured to femur 302, bearing assembly 304 can be mounted, removed, and replaced without removing anchor 34 by using fastener 40 in the manner previously discussed.

Similar to embodiments discussed previously that can be used on the proximal end of a tibia, it is appreciated that alternative embodiments of the present invention can also be used in replacing only a single condyle at the distal end of femur 302. A femoral uni-condylar implant can be replaced with a total condylar implant without removing anchor 34 in much the same way as discussed above regarding tibial implants 30 and 200.

Figure 15:
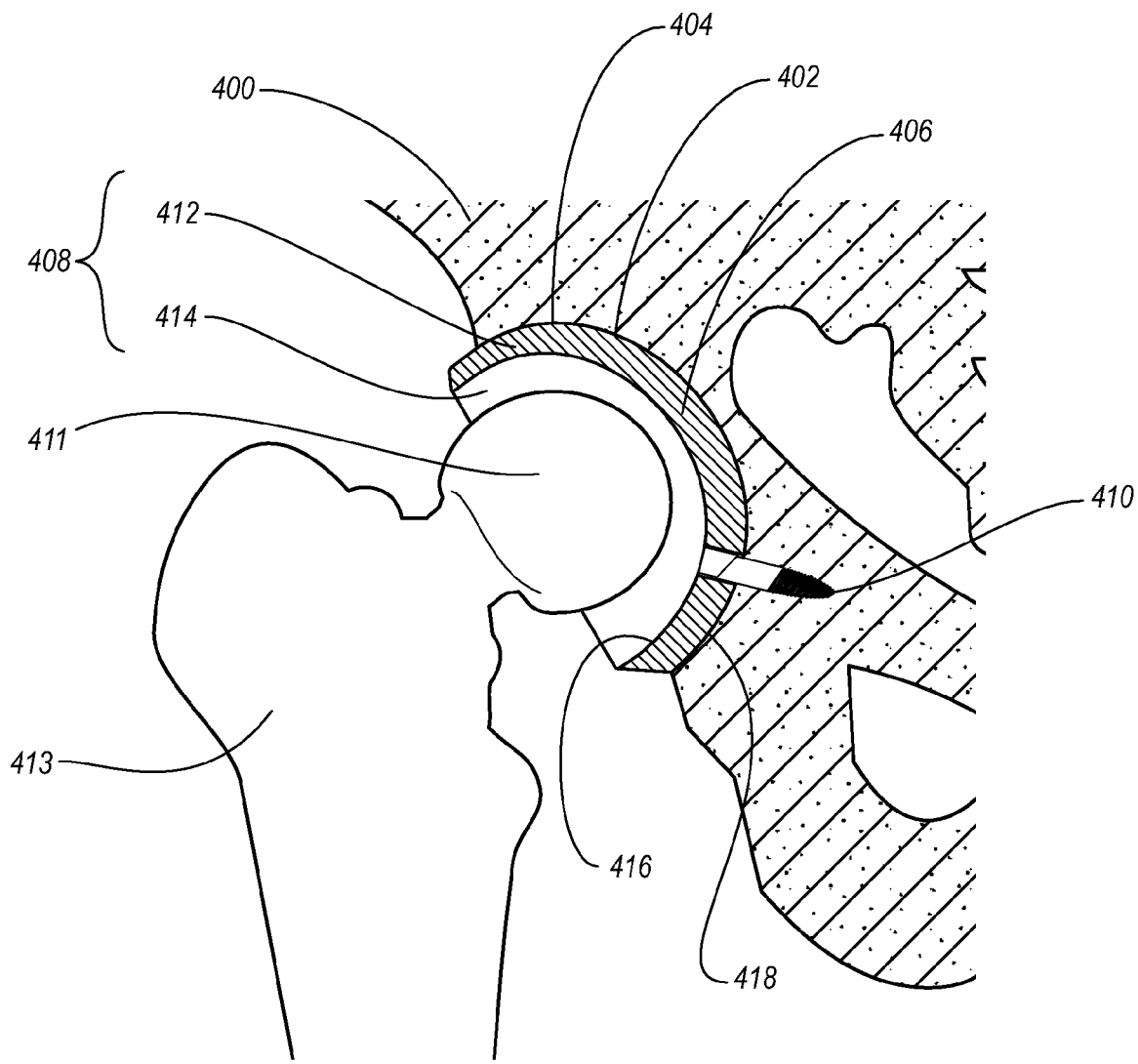
FIG. 15 is a cross-sectional side view of another alternative embodiment of an inventive implant mounted on a pelvis.

Embodiments of the present invention have been disclosed relating to both surfaces of a hinge type of joint, namely the tibia and femur. It is appreciated that the present invention can also be used with other hinge type joints, such as the elbow, or ball and socket joints, such as the hip joint. For example, depicted in FIG. 15 is a pelvis 400 that would normally include an acetabular socket 402 having an articulating surface. In the depicted drawing, acetabular socket 402 has been resected to form a resected articulating surface 404 and an implant 406 which incorporates features of the present invention has been mounted to pelvis 400 to replace acetabular socket 402.

Implant 406 comprises a bearing assembly 408 attached to an anchor 410 that is adapted for securing into pelvis 400. Similar to the acetabular socket that implant 406 is replacing, bearing assembly 408 is configured to receive a ball 411 at the proximal end of a femur 413 or a femoral implant. Towards this end, bearing assembly 408 comprises a roughly hemispherically shaped tray 412 (also known as a cup) and a bearing member 414 adapted for mounting thereon.

Tray 412 has a concave inside surface 416 and an opposing convex outside surface 418. Bearing member 414 mounts onto the inside surface 416 of tray 412, while outside surface 418 of tray 412 is disposed against pelvis 400. Bearing member 414 can be mounted to tray 412 in various ways. For example, similar to previously described embodiments, bearing member 414 and tray 412 can have matching mortices and tenons formed thereon which secure bearing member 414 to tray 412. Other methods of mounting can alternatively be used, such as using adhesives, snap fit connections, or other methods known in the art.

Figure 16:
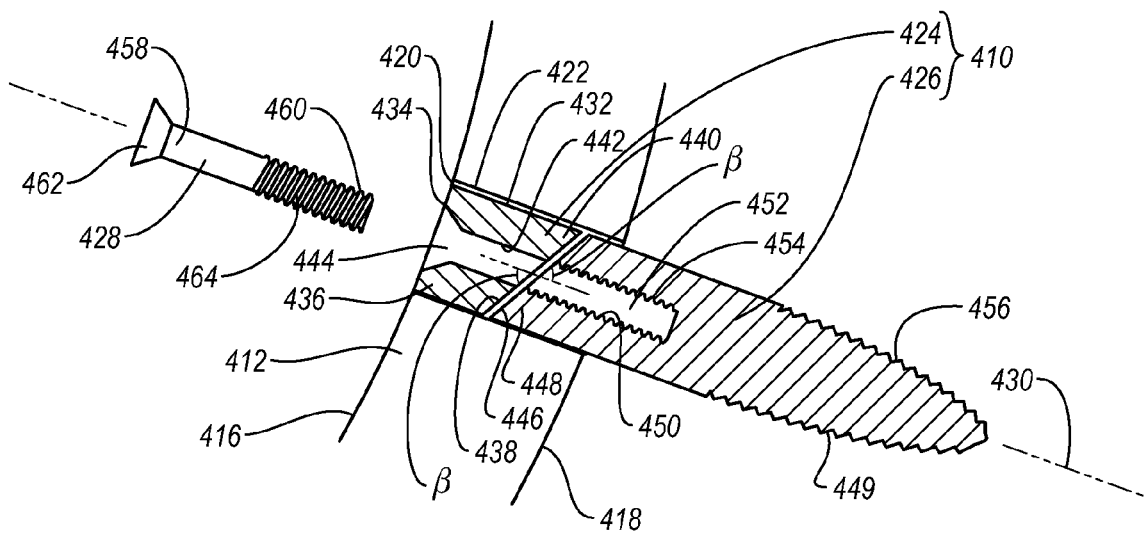
FIG. 16 is a cross-sectional side view of a partially assembled anchor used in the implant shown in FIG. 15.

Turning to FIG. 16 in conjunction with FIG. 15, similar to tray 36, tray 412 has an opening 420 bounded by a sidewall 422 which extends completely through tray 412 between inside surface 416 and outside surface 418. In the depicted embodiment, opening 420 is large enough for all of anchor 410 to completely pass through opening 420. Because of this, as with previously discussed embodiments of the current invention, once anchor 410 has been implanted and secured to pelvis 400, bearing assembly 408 can be mounted, removed, and replaced without removing anchor 410, as discussed below.

Anchor 410 projects away from outside surface 418 of tray 412 and is adapted to be inserted and secured in pelvis 400. Means for securing tray 412 to anchor 410 are provided. Similar to anchor 34, anchor 410 is used to secure implant 406 to pelvis 400. However, due to the shape of tray 412, it would be difficult to use the same type of fastener to secure tray 412 to anchor 410. That is, because tray 412 is rounded and fits within acetabular socket 402, it would be difficult for a physician to gain easy access to the side of implant 406 to push in or pull out a fastener from the side of anchor 410. Therefore an alternative means for securing is used with implant 406 according to the present invention.

As depicted in FIG. 16, anchor 410 is aligned along a longitudinal axis 430 and comprises a keel 424 with a stem 426 that projects outward therefrom. A locking screw 428 is used as a fastener to secure keel 424 to stem 426. In general, keel 424 has an external sidewall 432 which extends between a top surface 434 at a proximal end 436 and a spaced apart bottom surface 438 at a distal end 440. Top surface 434 and bottom surface 438 are generally planar. In one embodiment, keel 424 is positioned so that top surface 434 is generally orthogonal to axis 430, while bottom surface 438 is generally not orthogonal to axis 430. In one embodiment, an angle $\beta$ is formed between bottom surface 438 and axis 430 that is typically between about 15 degrees and about 75 degrees, with about 30 degrees to about 60 degrees being more common. Other angles can also be used. Keel 424 also has an interior surface 442 that bounds a smooth bore 444 extending through keel 424 between top surface 434 and bottom surface 438 along axis 430. The bore is enlarged at proximal end 436 of keel 424 to accommodate a head of locking screw 428, as discussed below.

Stem 426 is similar to stem 96, except that stem 426 has no head formed thereon. Instead, stem 426 has a top surface 446 formed at a proximal end 448 thereof from which a threaded shank 449 extends. Top surface 446 of stem 426 is shaped to match bottom surface 438 of keel 424. That is, top surface 446 of stem 426 is generally planar and generally at the same angle β to axis 430 as is bottom surface 438 of keel 424. Stem 426 has an interior surface 450 that bounds a passageway or bore 452 extending into stem 426 from top surface 446 along axis 430. Bore 452 includes internal threads 454 to engage locking screw 428 and is generally longitudinally aligned with bore 444 of keel 424 along axis 430. Similar to shank 132, shank 449 tapers to a point at a distal end 456 of stem 426 along axis 430 and has threads formed thereon so that shank 449 can be threaded or screwed into pelvis 400 so as to securely engage pelvis 400.

Locking screw 428 extends between a proximal end 458 and a spaced apart distal end 460, a head 462 being formed at proximal end 458 and external threads 464 being formed at distal end 460. External threads 464 match the internal threads 454 of bore 452, thus allowing locking screw 428 to be able to be screwed into stem 426. Formed on head 462 are means for engagement, such as, for example, a slot, a socket, or other configurations known in the art. The use of a screwdriver, Allen wrench, or other type of tool known in the art for rotating a screw and corresponding to the means for engagement can be used to screw locking screw 428 into stem 426.

As depicted in FIG. 16, to secure tray 412 to pelvis anchor 410, tray 412 is placed over stem 426 such that opening 420 aligns with top surface 446 of stem 426. Tray 412 is then mounted onto pelvis 400 such that proximal end 448 of stem 426 is at least partially disposed within opening 420. Keel 424 is placed within opening 420 such that distal end 440 of keel 424 biases against proximal end 448 of stem 426 so that the angle of bottom surface 438 of keel 424 matches the angle of top surface 446 of stem 426.

Figure 17:
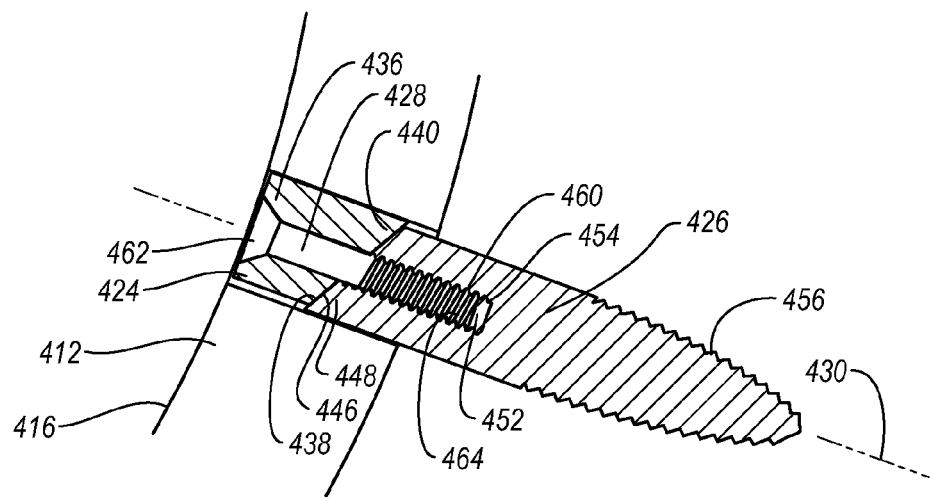
FIG. 17 is a cross-sectional side view of the anchor shown in FIG. 15, fully assembled.

Turning to FIG. 17, distal end 460 of locking screw 428 is then inserted through bore 444 of keel 424 and screwed into bore 452 of stem 426. As locking screw 428 is rotated in one direction, the external threads 464 of locking screw 428 engage the internal threads 454 within bore 452, pulling locking screw 428 further towards distal end 456 of stem 426. As locking screw 428 is screwed into stem 426, head 462 of locking screw 428 biases against the enlarged portion of bore 444 at proximal end 436 of keel 424 and causes keel 424 to push against stem 426. As bottom surface 438 of keel 424 pushes against top surface 446 of stem 426, the angling of the surfaces 438, 446 causes distal end 440 of keel 424 and proximal end 448 of stem 426 to push outward against sidewall 422 of tray 412 in opposite directions as shown in FIG. 17, thereby securing tray 412 to stem 426.

Alternatively, bore 444 of keel 424 can be slightly offset longitudinally from bore 452 of stem 426. Then, when locking screw 428 is screwed into stem 426, the longitudinal offset will cause distal end 440 of keel 424 and proximal end 448 of stem 426 to push outward against sidewall 422 of tray 412 in opposite directions, thereby securing tray 412 to stem 426.

To remove tray 412 from pelvis 400, locking screw 428 is at least partially unscrewed from stem 426 by rotating locking screw 428 in a direction opposite to the direction used in tightening locking screw 428. This causes the force pushing keel 424 and stem 426 together to lessen. When this occurs, distal end 440 of keel 424 and proximal end 448 of stem 426 stop pushing outward against sidewall 422 of tray 412 thus releasing the secure connection between tray 412 and anchor 410. Tray 412 can then be lifted off stem 426 and keel 424 to be removed from pelvis 400.

The aforementioned methods of securing and removing tray 412 from pelvis 400 allows for easy replacement of implant 406 using the same anchor 410 when, for example, a tray is damaged, or a different sized tray is desired (due to growth in a child, for example).

It is appreciated that the present invention can also be used with other joints within the body, such as the shoulder, elbow, ankle, wrist, or the like.

In view of the foregoing, different embodiments of the present invention have a number of benefits. For example, because of the mechanism for mounting, it can be relative easy to adjust position or orientation of the tray and bearing member. The present invention also permits a single anchoring system to be used for both a uni-condylar implant and a total condylar implant. The switch between the two implants can be made without having to remove the anchor from the bone. Thus, the inventive system and method can decrease material costs, reduce the surgical time for the procedure, and minimize bone damage.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An implant for mounting on a resected articulation surface of a bone, the implant comprising:
 a tray having a top surface and an opposing bone apposition surface with a perimeter edge extending therebetween, an opening extending completely through the tray between the top surface and the bone apposition surface, and a first passageway extending from the perimeter edge to the opening;
 a bearing member mounted on the top surface of the tray, the bearing member having a top articular surface;
 an anchor projecting away from the bone apposition surface of the tray, the anchor comprising:
  a keel having a top surface and a bottom surface, an opening extending through the keel between the top surface and bottom surface, and a keel passageway extending transversely through the keel; and
  an elongated stem releasably attached to the keel, the elongated stem being adapted to engage the bone, and the anchor being configured so that the entire anchor can pass completely through the opening of the tray; and
 a fastener sized to pass into the first passageway and into the keel passageway when the keel is disposed in the opening of the tray, so that the fastener removably secures the tray to the anchor.

2. The implant of claim 1, wherein the tray includes a second passageway extending away from the opening of the tray and the first opening, so that the first passageway, the second passageway and the keel passageway align to form a combined passageway when the keel is disposed in the opening of the tray, the fastener being disposed within the combined passageway to removably secure the tray to the anchor.

3. The implant of claim 1, wherein the fastener comprises a top surface and an opposing bottom surface that are in diverging planes.

4. The implant of claim 1, wherein the bearing member is removably mounted on the top surface of the tray.

5. The implant of claim 1, further comprising at least one projection extending downwardly from the bone apposition surface of the tray.

6. The implant of claim 1, wherein the implant is a unicondylar implant.

7. The implant of claim 1, wherein the implant is a total condylar implant.

8. The implant of claim 1, wherein the anchor has a central longitudinal axis, the anchor projecting away from the bone apposition surface of the tray so as to form an inside angle between the central longitudinal axis of the anchor and the bone apposition surface of the tray that is less than about 80°.

9. The implant of claim 1, wherein the stem of the anchor comprises a threaded distal portion that is adapted to thread into the bone so as to engage the bone.

10. The implant of claim 1, wherein
the keel is removably secured to the tray by the fastener; and wherein
the elongated stem has a threaded distal portion adapted to thread into bone and an opposing threaded proximal portion at least partially disposed within the opening on the keel; and wherein
the anchor further comprises a nut threaded onto the threaded proximal portion of the stem so as to secure the stem to the keel.

11. The implant of claim 1, wherein the implant is configured to mount to a proximal end of a tibia and replace a condyle thereon.

12. An implant for mounting on a resected articulation surface of a bone, the implant comprising:
a tray having a top surface and opposing bone apposition surface with a perimeter edge extending therebetween, an opening extending completely through the tray between the top surface and the bone apposition surface, and a first passageway extending from the perimeter edge to the opening;
a bearing member removably mounted on the top surface of the tray, the bearing member having a top articular surface;
a keel having a top surface and a bottom surface, an opening extending through the keel between the top surface and bottom surface, and a keel passageway extending transversely through the keel, the keel sized so that the entire keel can pass completely through the opening of the tray;
a fastener sized to pass into the first passageway and into the keel passageway when the keel is disposed in the opening of the tray, so that the fastener removably secures the tray to the keel;
an elongated stem having a threaded distal portion adapted to thread into bone and an opposing threaded proximal portion at least partially disposed within the opening of the keel; and
a nut threaded onto the threaded proximal portion of the stem so as to secure the stem to the keel, the nut being a separate and distinct element from the keel.

13. The implant of claim 12, further comprising means for coupling a driver to the proximal end of the stem.

14. The implant of claim 13, wherein the means for coupling comprises the proximal end of the stem terminating at a proximal end face, a socket being formed on the proximal end face that is adapted to receive a driver.

15. An implant for mounting on a resected articulation surface of a bone, the implant comprising:
a tray having a perimeter edge extending between a top surface and an opposing bone apposition surface, the tray having an opening extending therethrough between the top surface and the opposing bone apposition surface, the tray also having a first passageway extending from the perimeter edge to the opening;
a bearing member removably mounted on the top surface of the tray, the bearing member having a top articular surface;
a keel sized to pass completely through the opening of the tray, the keel having a keel passageway extending transversely therethrough, the keel passageway aligning with the first passageway when the keel is disposed within the opening of the tray, the keel sized so that the entire keel can pass completely through the opening of the tray;
an elongated stem having a threaded distal portion adapted to thread into bone and an opposing proximal portion, the proximal portion of the stem being releasably secured to the keel; and
a fastener inserted into the first passageway and the second passageway when the keel is disposed in the opening of the tray, so that the fastener secures the tray to the keel.

16. The implant of claim 15, further comprising a nut that threads onto the proximal portion of the stem to releasably secure the stem to the keel.

17. The implant of claim 15, wherein the keel has an opening extending therethrough that intersects with the second passageway, the stem being at least partially disposed within the opening of the keel.

18. The implant of claim 15, wherein the tray includes a second passageway extending away from the opening of the tray and the first opening, so that the first passageway, the second passageway and the keel passageway align to form a combined passageway when the keel is disposed in the opening of the tray, the fastener being disposed within the combined passageway to removably secure the tray to the keel.

* * * * *